US009878916B2

(12) United States Patent
Elomari

(10) Patent No.: US 9,878,916 B2
(45) Date of Patent: Jan. 30, 2018

(54) SYNTHESIS OF MOLECULAR SIEVE SSZ-63

(71) Applicant: Chevron U.S.A. Inc., San Ramon, CA (US)

(72) Inventor: Saleh Ali Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/433,075

(22) Filed: Feb. 15, 2017

(65) Prior Publication Data
US 2017/0341947 A1 Nov. 30, 2017

Related U.S. Application Data
(60) Provisional application No. 62/341,693, filed on May 26, 2016.

(51) Int. Cl.
C01B 39/48 (2006.01)
B01J 29/70 (2006.01)
C07D 207/06 (2006.01)

(52) U.S. Cl.
CPC .............. *C01B 39/48* (2013.01); *B01J 29/70* (2013.01); *C07D 207/06* (2013.01); *C01P 2002/72* (2013.01); *C01P 2004/03* (2013.01)

(58) Field of Classification Search
CPC .................................. C01B 39/48; B01J 29/70
See application file for complete search history.

(56) References Cited

U.S. PATENT DOCUMENTS 6,733,742 B1 5/2004 Elomari
2002/0081262 A1 6/2002 Elomari
2017/0341947 A1* 11/2017 Elomari .................. C01B 39/48

FOREIGN PATENT DOCUMENTS

WO 2016048406 3/2016

OTHER PUBLICATIONS

J.B. Higgins, R.B. Lapierre, J.L. Schlenker, A.C. Rohrman, J.D. Wood, G.T.Kerr and W.J. Rohrbaugh "The Framework Topology of Zeolite Beta" Zeolites, 1988, 8, 446-452.
J.B. Higgins, R.B. Lapierre, J.L. Schlenker, A.C. Rohrman, J.D. Wood, G.T.Kerr and W.J. Rohrbaugh "The Framework Topology of Zeolite Beta—A Correction" Zeolites, 1989, 9, 358.
A.W. Burton, S. Elomari, I. Chan, A. Pradhan and C. Kibby "Structure and Synthesis of SSZ-63: Toward an Ordered Form of Zeolite Beta" J. Phys. Chem. B 2005, 109, 20266-20275.
International Search Report, International Appl. No. PCT/US2017/017973, dated Apr. 20, 2017.

* cited by examiner

Primary Examiner — David M Brunsman
(74) Attorney, Agent, or Firm — Terrence M. Flaherty

(57) ABSTRACT

A method is disclosed for synthesizing molecular sieve SSZ-63 using 1-(decahydronaphthalen-2-yl)-1-methylpyrrolidinium cations as a structure directing agent.

10 Claims, 8 Drawing Sheets

SYNTHESIS OF MOLECULAR SIEVE SSZ-63

TECHNICAL FIELD

The present disclosure is directed to a method of synthesizing zeolite SSZ-63 using 1-(decahydronaphthalen-2-yl)-1-methylpyrrolidinium cations as a structure directing agent.

BACKGROUND

Molecular sieves are a commercially important class of crystalline materials. They have distinct crystal structures with ordered pore structures which are demonstrated by distinct X-ray diffraction patterns. The crystal structure defines cavities and pores which are characteristic of the different species. Molecular sieves such as zeolites have been used extensively to catalyze a number of chemical reactions in refinery and petrochemical reactions, and catalysis, adsorption, separation, and chromatography.

U.S. Pat. No. 6,733,742 discloses molecular sieve SSZ-63 and its synthesis using N-cyclodecyl-N-methylpyrrolidinium cations as a structure directing agent. SSZ-63 is structurally related to zeolite beta. The structure of conventional zeolite beta may be described as a random intergrowth of two polytypes, polytype A and polytype B, in nearly equal proportions. A. W. Burton et al. (*J. Phys. Chem. B* 2005, 109, 20266-20275) report that SSZ-63 may be described as a random intergrowth of beta polytypes B and $C_H$ having about 60-70% polytype $C_H$ character. Polytype $C_H$ is the hypothetical polytype C proposed by J. B. Higgins et al. (*Zeolites,* 1988, 8, 446-452 and *Zeolites,* 1989, 9, 358) and is essentially an ordered intergrowth of polytypes A and B.

The commercial development of SSZ-63 has been hindered by the high cost of the N-cyclodecyl-N-methylpyrrolidinium cation structure directing agent required in U.S. Pat. No. 6,733,742 for its synthesis and, hence, there has been significant interest in finding alternative, less expensive structure directing agents for the synthesis of SSZ-63.

According to the present disclosure, molecular sieve SSZ-63 has now been synthesized using 1-(decahydronaphthalen-2-yl)-1-methylpyrrolidinium cations as a structure directing agent.

SUMMARY

In one aspect, there is provided a method of synthesizing a molecular sieve having the framework structure of SSZ-63, the method comprising: (a) preparing a reaction mixture comprising: (1) a source of silicon oxide; (2) a source of an oxide of a trivalent element (e.g., one or more of boron, aluminum, gallium, and iron); (3) a source of a Group 1 or 2 metal; (4) a structure directing agent comprising 1-(decahydronaphthalen-2-yl)-1-methylpyrrolidinium cations; (5) hydroxide ions; and (6) water; and (b) subjecting the reaction mixture to crystallization conditions sufficient to form crystals of the molecular sieve.

In another aspect, there is provided a molecular sieve having the framework structure of SSZ-63 and comprising 1-(decahydronaphthalen-2-yl)-1-methylpyrrolidinium cations in its pores.

In yet another aspect, there is provided an organic nitrogen-containing compound comprising a cation having the following structure (1):

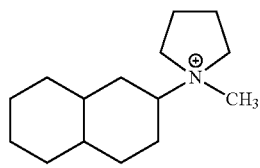

DETAILED DESCRIPTION

Introduction

Figure 1:
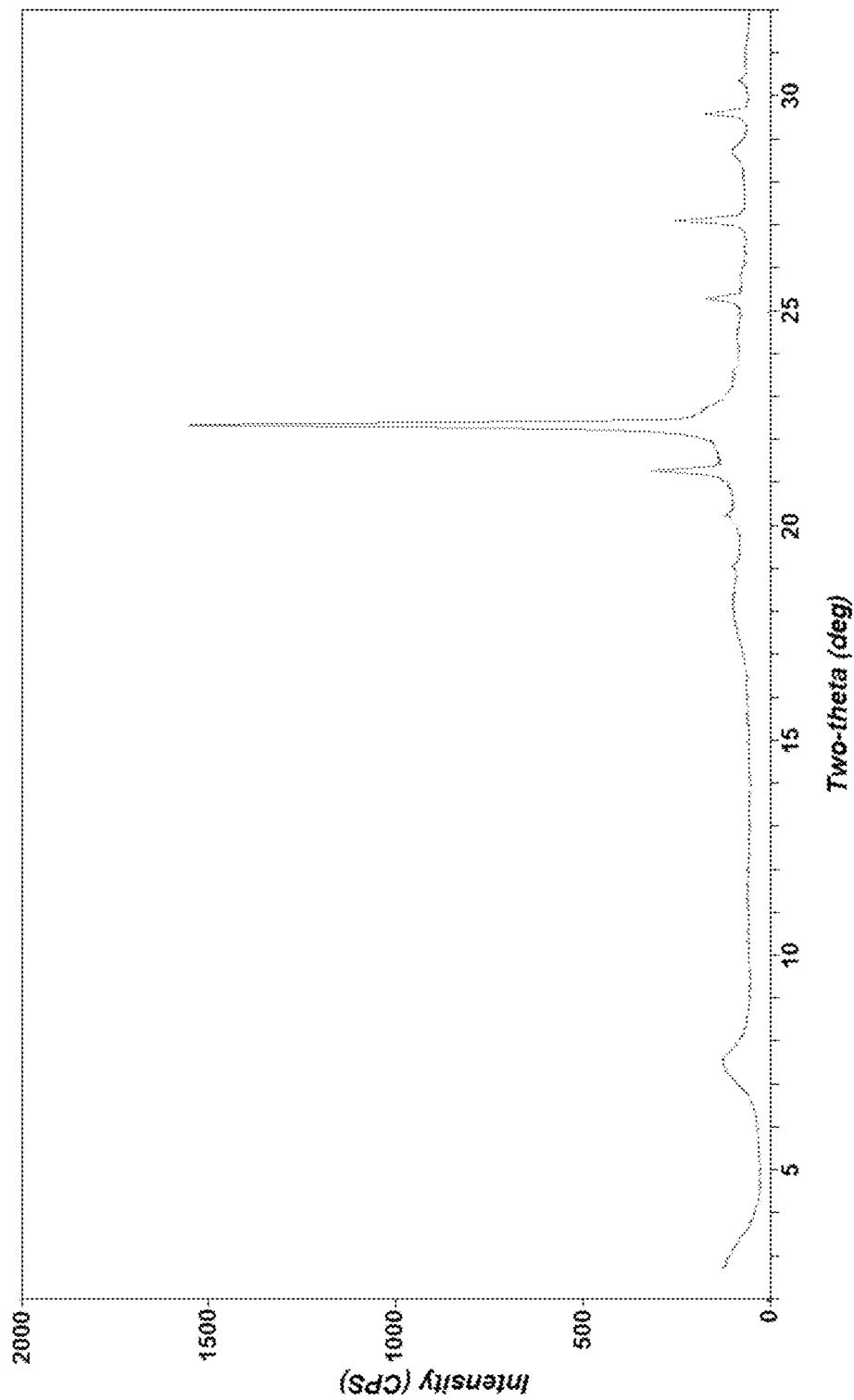
FIG. 1 is a powder X-ray diffraction (XRD) pattern of the as-synthesized borosilicate molecular sieve prepared in Example 2.

The term "as-synthesized" is employed herein to refer to a molecular sieve in its form after crystallization, prior to removal of the structure directing agent.

The term "anhydrous" is employed herein to refer to a molecular sieve substantially devoid of both physically adsorbed and chemically adsorbed water.

As used herein, the numbering scheme for the Periodic Table Groups is as disclosed in *Chem. Eng. News* 1985, 63(5), 26-27.

Reaction Mixture

In general, molecular sieve SSZ-63 is synthesized by: (a) preparing a reaction mixture comprising: (1) a source of silicon oxide; (2) a source of an oxide of a trivalent element (X); (3) a source of a Group 1 or 2 metal (M); (4) a structure directing agent (Q) comprising 1-(decahydronaphthalen-2-yl)-1-methylpyrrolidinium cations; (5) hydroxide ions; and (6) water; and (b) subjecting the reaction mixture to crystallization conditions sufficient to form crystals of the molecular sieve.

The composition of the reaction mixture from which the molecular sieve is formed, in terms of molar ratios, is identified in Table 1 below:

TABLE 1

| Reactants | Useful | Exemplary |
|---|---|---|
| $SiO_2/X_2O_3$ | 10 to 200 | 15 to 100 |
| $M/SiO_2$ | 0.05 to 0.40 | 0.10 to 0.30 |
| $Q/SiO_2$ | 0.05 to 0.50 | 0.10 to 0.30 |
| $OH/SiO_2$ | 0.10 to 0.50 | 0.15 to 0.40 |
| $H_2O/SiO_2$ | 10 to 80 | 15 to 60 | wherein X, M and Q and are as described herein above.

Suitable sources of silicon oxide include colloidal silica, fumed silica, precipitated silica, alkali metal silicates, and tetraalkyl orthosilicates.

Suitable sources of the trivalent element X depend on the element X selected. Where X is boron, suitable sources of boron oxide include boric acid and water-soluble boric acid salts. Where X is aluminum, suitable sources of aluminum oxide include zeolite Y, hydrated alumina and water-soluble aluminum salts (e.g., aluminum nitrate).

Examples of suitable Group 1 or Group 2 metals (M) include sodium, potassium and calcium, with sodium being preferred. The metal (M) is preferably present in the reaction mixture as the hydroxide.

The structure directing agent (Q) comprises 1-(decahydronaphthalen-2-yl)-1-methylpyrrolidinium cations, represented by the following structure (1):

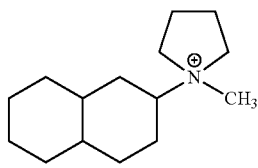

(1)

Suitable sources of Q are the hydroxides, chlorides, bromides, and/or other salts of the quaternary ammonium compound.

The reaction mixture may also contain seeds of a molecular sieve material, such as SSZ-63 from a previous synthesis, desirably in an amount of from 0.01 to 10,000 ppm by weight (e.g., from 100 to 5000 ppm by weight) of the reaction mixture.

For each embodiment described herein, the reaction mixture can be supplied by more than one source. Also, two or more reaction components can be provided by one source.

The reaction mixture can be prepared either batch wise or continuously. Crystal size, morphology and crystallization time of the crystalline molecular sieve described herein can vary with the nature of the reaction mixture and the crystallization conditions.

Crystallization and Post-Synthesis Treatment

Crystallization of the molecular sieve from the above reaction mixture can be carried out under either static, tumbled or stirred conditions in a suitable reactor vessel, such as for example polypropylene jars or Teflon-lined or stainless steel autoclaves, at a temperature of from 125° C. to 200° C. for a time sufficient for crystallization to occur at the temperature used, e.g., from 5 to 20 days. Crystallization is usually carried out in a closed system under autogenous pressure.

Once the molecular sieve crystals have formed, the solid product is separated from the reaction mixture by standard mechanical separation techniques such as centrifugation or filtration. The crystals are water-washed and then dried to obtain the as-synthesized molecular sieve crystals. The drying step is typically performed at a temperature of less than 200° C.

As a result of the crystallization process, the recovered crystalline molecular sieve product contains within its pore structure at least a portion of the structure directing agent used in the synthesis.

The present molecular sieve may be subjected to treatment to remove part or all of the organic structure directing agent used in its synthesis. This is conveniently effected by thermal treatment in which the as-synthesized material is heated at a temperature of at least about 370° C. for at least 1 minute and generally not longer than 20 hours. The thermal treatment can be performed at a temperature up to 925° C. While sub-atmospheric pressure can be employed for the thermal treatment, atmospheric pressure is desired for reasons of convenience. Additionally or alternatively, the organic structure directing agent can be removed by treatment with ozone (see, e.g., A. N. Parikh et al., Micropor. Mesopor. Mater. 2004, 76, 17-22).

To the extent desired, the original Group 1 or 2 metal cations in the molecular sieve can be replaced in accordance with techniques well known in the art by ion exchange with other cations. Illustrative examples of suitable replacing cations include metal ions, hydrogen ions, hydrogen precursor ions (e.g., ammonium ions), and mixtures thereof. Particularly preferred replacing cations include hydrogen, rare earth metals and metals of Groups 2 to 15 of the Periodic Table of the Elements.

Characterization of the Molecular Sieve

In its as-synthesized and anhydrous form, the present molecular sieve has a chemical composition, in terms of molar ratios, as described in Table 2:

TABLE 2

|  | Broad | Exemplary |
| --- | --- | --- |
| $SiO_2/X_2O_3$ | 10 to 200 | 15 to 100 |
| $Q/SiO_2$ | >0 to 0.2 | >0 to 0.1 |
| $M/SiO_2$ | >0 to 0.2 | >0 to 0.1 | wherein X is a trivalent element (e.g., one or more of boron, aluminum, gallium, and iron, especially one or more of boron and aluminum); Q comprises 1-(decahydronaphthalen-2-yl)-1-methylpyrrolidinium cations; and M is a Group 1 or 2 metal.

It should be noted that the as-synthesized form of the molecular sieve described herein may have molar ratios different from the molar ratios of reactants of the reaction mixture used to prepare the as-synthesized form. This result may occur due to incomplete incorporation of 100% of the reactants of the reaction mixture into the crystals formed (from the reaction mixture).

In its calcined from, the present molecular sieve has a chemical composition comprising the following molar relationship:

$$X_2O_3:(n)SiO_2$$

wherein X is a trivalent element (e.g., one or more of boron, aluminum, gallium, and iron, especially one or more of boron and aluminum); and n has a value from of 10 to 200 (e.g., 10 to 100, 10 to 75, 15 to 200, 15 to 100, 15 to 75, 20 to 200, 20 to 100, 20 to 75, 25 to 200, 25 to 100, 25 to 75, 30 to 200, 30 to 100, or 30 to 75).

As taught by U.S. Pat. No. 6,733,742, molecular sieve SSZ-63 is characterized by a powder X-ray diffraction pattern which, in the as-synthesized form of the molecular sieve, includes at least the peaks set forth in Table 3 below and which, in the calcined form of the molecular sieve, includes at least the peaks set forth in Table 4 below.

TABLE 3

Characteristic Peaks for As-Synthesized SSZ-63

| 2-Theta[a] | d-spacing (nm) | Relative Intensity[b] |
|---|---|---|
| 7.17 | 1.232 | W |
| 7.46 | 1.184 | W |
| 7.86 | 1.124 | W |
| 8.32 | 1.062 | W |
| 21.42 | 0.415 | M |
| 22.46 | 0.396 | VS |
| 22.85 | 0.389 | W |
| 25.38 | 0.351 | W |
| 27.08 | 0.329 | W |
| 29.62 | 0.301 | W |

[a]±0.2
[b]The powder X-ray diffraction patterns provided are based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

TABLE 4

Characteristic Peaks for Calcined SSZ-63

| 2-Theta[a] | d-spacing (nm) | Relative Intensity[b] |
|---|---|---|
| 7.19 | 1.229 | M |
| 7.42 | 1.191 | VS |
| 7.82 | 1.130 | VS |
| 8.30 | 1.064 | M |
| 13.40 | 0.660 | M |
| 21.46 | 0.414 | W |
| 22.50 | 0.395 | VS |
| 22.81 | 0.390 | W |
| 27.14 | 0.328 | M |
| 29.70 | 0.306 | W |

[a]±0.2
[b]The powder X-ray diffraction patterns provided are based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

The powder X-ray diffraction patterns presented herein were collected by standard techniques. The radiation was CuK$_\alpha$ radiation. The peak heights and the positions, as a function of 2θ where θ is the Bragg angle, were read from the relative intensities of the peaks, and d, the interplanar spacing corresponding to the recorded lines, can be calculated.

Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can result from variations in the organic compound used in the preparation. Calcination can also cause minor shifts in the X-ray diffraction pattern.

EXAMPLES

The following illustrative examples are intended to be non-limiting.

Example 1

Synthesis of 1-(decahydronaphthalen-2-yl)-1-methylpyrrolidinium hydroxide

A three-necked round bottom flask equipped with a reflux condenser and a mechanical stirrer was charged with a solution of an isomeric mixture of cis- and trans-2-decalone (50 g, 0.33 mole) in anhydrous cyclohexane (450 mL). Then, pyrrolidine (60 g, 0.84 mole) and anhydrous magnesium sulfate (60 g, 0.5 mole) were added to the solution. The resulting mixture was stirred while heating at reflux for 4 days. To ensure complete conversion of 2-decalone, additional pyrrolidine (20 g) was added and the reaction mixture was allowed to further stir at reflux for an additional 48 hours. The reaction mixture was filtered through a fritted-glass funnel. The filtrate was concentrated at reduced pressure on a rotary evaporator to give an isomeric mixture of the expected enamine, 1-(octahydronaphthalen-2-yl)-pyrrolidine (61 g, ~90% yield), as a reddish oily substance. The product was confirmed by $^1$H- and $^{13}$C-NMR spectroscopy. The enamine was then reduced to the corresponding amine, 1-(decahydronaphthalen-2-yl)pyrrolidine, in 98% yield via catalytic hydrogenation in the presence of 10% Pd on activated carbon at a hydrogen pressure of 55 psi in ethanol.

To a solution of 1-(decahydronaphthalen-2-yl)pyrrolidine (45 g, 0.22 mole) in anhydrous methanol (300 mL) in a 1-L 3-neck reaction flask, methyl iodide (50 g, 0.35 mole) was added. The reaction mixture was stirred at room temperature with an overhead stirrer for 48 hours. Then, an additional ¼ mole equivalent of methyl iodide was added and the reaction mixture was stirred while heating at reflux for 90 minutes. The reaction mixture was then cooled to room temperature and concentrated under reduced pressure on a rotary evaporator to remove the solvent and excess methyl iodide. The reaction afforded the desired product as a tan solid material in 98% yield (75.3 g). The solid product was purified by dissolving in hot isopropyl alcohol (50 mL) and then was allowed to recrystallize. The re-crystallization yielded a mixture of cis/trans isomers of 1-(decahydronaphthalen-2-yl)-1-methylpyrrolidinum iodide (73 g) as an off-while solid. The product was confirmed by $^1$H- and $^{13}$C-NMR spectroscopy.

Then, 1-(decahydronaphthalen-2-yl)-1-methylpyrrolidinum iodide was ion-exchanged to the corresponding 1-(decahydronaphthalen-2-yl)-1-methylpyrrolidinum hydroxide by dissolving 1-(decahydronaphthalen-2-yl)-1-methylpyrrolidinum iodide (70 g, 0.20 mole) in deionized water (250 mL) in a 500 mL polyvinyl plastic bottle. To the solution, BIO-RAD AH1-X8 ion-exchange resin-OH (225 g) was added and the mixture was gently stirred at room temperature overnight. The mixture was filtered and the solids were rinsed with deionized water (75 mL). The reaction afforded 0.19 mole (0.58 M solution) of the templating agent, 1-(decahydronaphthalen-2-yl)-1-methylpyrrolidinum hydroxide, as indicated by titration analysis with 0.1N HCl.

Scheme A below depicts the synthesis of 1-(decahydronaphthalen-2-yl)-1-methylpyrrolidinium hydroxide.

SCHEME A

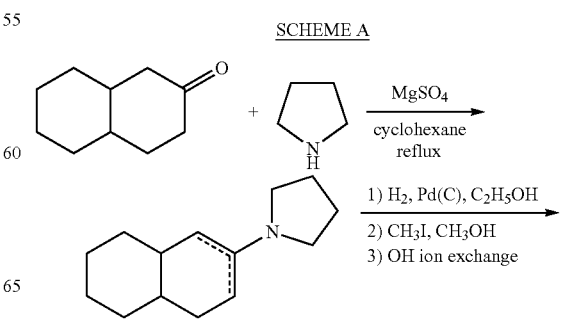

-continued

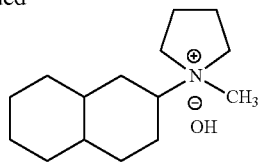

Example 2

Synthesis of Borosilicate SSZ-63 (B-SSZ-63)

A 23 cc Teflon liner was charged with a 0.58 M solution of 1-(decahydronaphthalen-2-yl)-1-methylpyrrolidinum hydroxide (5.2 g), a 1N NaOH solution (1.22 g) and deionized water (5.6 g). To this mixture, $Na_2B_4O_7 \cdot 10H_2O$ (63 mg) was added and stirred until dissolved. Then, CAB-O-SIL® M-5 fumed silica (0.92 g) was added and stirred until a homogeneous mixture was achieved. The liner was capped and placed in a Parr autoclave and heated in an oven at 160° C. while tumbling at about 43 rpm. The progress of the crystallization was monitored periodically by SEM. Once the crystallization was completed (6-12 days), the reaction mixture was filtered using a fritted-glass funnel. The obtained solids were thoroughly rinsed with deionized water and dried in oven at 120° C.

Figure 2:
FIG. 2 is a Scanning Electron Micrograph (SEM) image of the as-synthesized borosilicate molecular sieve prepared in Example 2.

The resulting as-synthesized product was analyzed by powder XRD and SEM. FIG. 1 is the powder XRD pattern of the product, which showed the product to be SSZ-63. Table 5 below shows the powder XRD lines for the product. FIG. 2 shows a SEM image of the product. The reaction afforded about 0.9 g of dry borosilicate SSZ-63.

TABLE 5

| 2-Theta | d-spacing (nm) | Relative Intensity[a] |
|---|---|---|
| 7.62 | 1.160 | M |
| 20.24 | 0.438 | W |
| 21.27 | 0.417 | W |
| 22.35 | 0.397 | VS |
| 25.28 | 0.352 | W |
| 27.09 | 0.329 | W |
| 29.58 | 0.302 | W |
| 30.36 | 0.294 | W |
| 33.37 | 0.268 | W |
| 34.79 | 0.258 | W |

[a]The powder X-ray diffraction patterns provided are based on a relative intensity scale in which the strongest line in the XRD pattern is assigned a value of 100: W = weak (>0 to ≤20); M = medium (>20 to ≤0); S = strong (>40 to ≤60); VS = very strong (>60 to ≤100).

Example 3

Synthesis of Aluminosilicate SSZ-63 (Al-SSZ-63)

A 23 cc Teflon liner was charged with a 0.58M aqueous solution of 1-(decahydronaphthalen-2-yl)-1-methylpyrrolidinum hydroxide (3.9 g, 2.25 mmole), a 1M aqueous solution of NaOH (1.5 g) and deionized water (4.5 g). To this mixture, Rehies F-2000 aluminum hydroxide (34 mg) was added and stirred until all dissolved. Then, CAB-O-SIL® M-5 fumed silica (0.92 g) was added and thoroughly stirred until a homogenous mixture was obtained. The resulting gel was capped off and placed in a Parr steel autoclave and heated in an oven at about 170° C. while tumbling at about 43 rpm. The reaction was followed by periodically monitoring the pH of the gel, and by looking for crystal growth using SEM. Once the crystallization was completed, after heating for 9-12 days at the conditions described above, the starting reaction gel turned into a clear liquid layer and a fine powdery precipitate. The mixture was filtered through a fritted-glass funnel. The collected solids were thoroughly washed with deionized water and, then, rinsed with acetone (~20 mL) to remove any organic residues. The solids were allowed to air-dry overnight and, then, dried in an oven at 120° C. for 1 hour.

Figure 3:
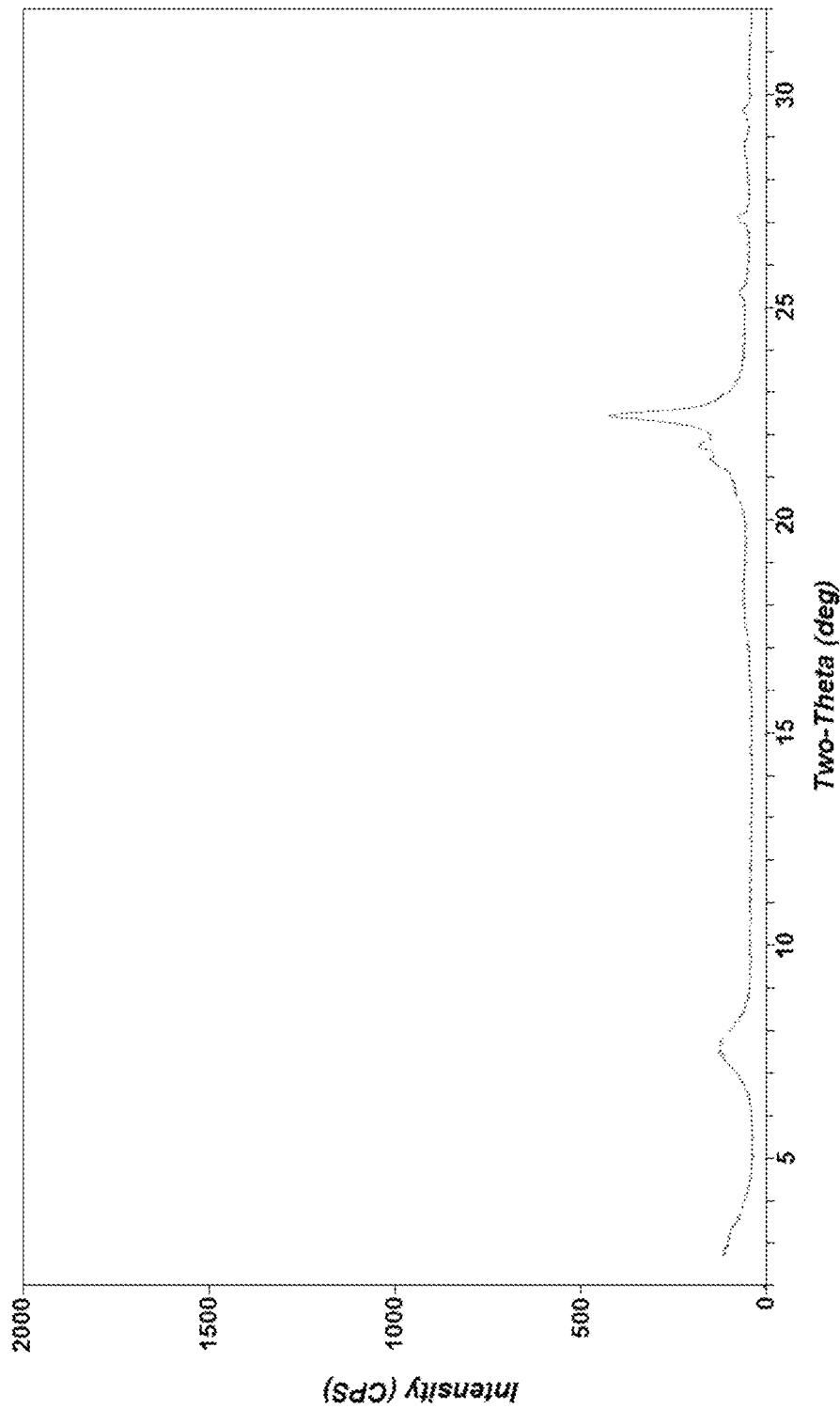
FIG. 3 is a powder XRD pattern of the as-synthesized aluminosilicate molecular sieve prepared in Example 3.
Figure 4:
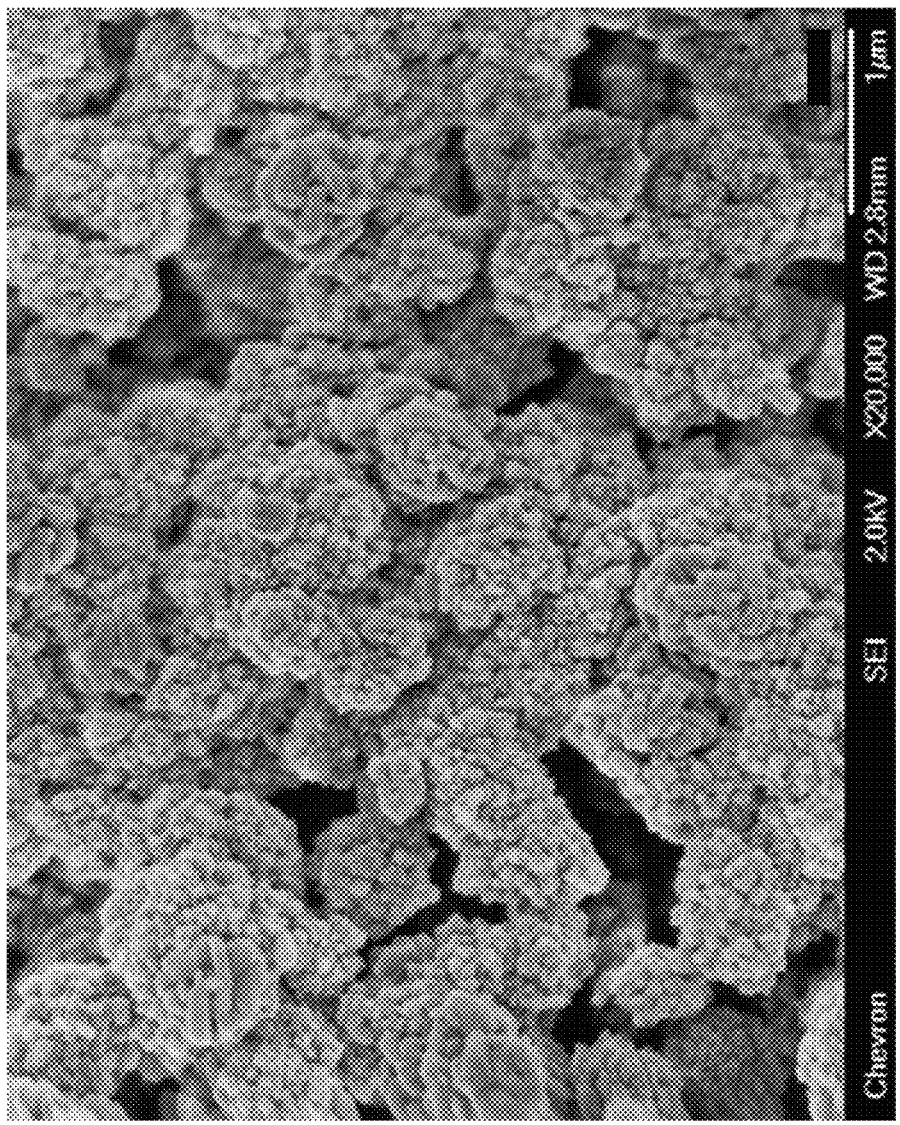
FIG. 4 is a SEM image of the as-synthesized aluminosilicate molecular sieve prepared in Example 3.

The resulting as-synthesized product was analyzed by powder XRD and SEM. FIG. 3 is the powder XRD pattern of the product, which showed the product to be SSZ-63. Table 6 below shows the powder XRD lines for the product. FIG. 4 shows a SEM image of the product.

TABLE 6

| 2-Theta | d-spacing (nm) | Relative Intensity[a] |
|---|---|---|
| 7.62 | 1.159 | M |
| 20.72 | 0.429 | W |
| 21.39 | 0.415 | M |
| 21.76 | 0.408 | S |
| 22.44 | 0.396 | VS |
| 25.29 | 0.352 | W |
| 27.12 | 0.329 | W |
| 28.84 | 0.309 | W |
| 29.60 | 0.302 | W |
| 33.49 | 0.267 | W |
| 35.95 | 0.250 | W |

[a]The powder X-ray diffraction patterns provided are based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

Example 4

Synthesis of Al-SSZ-63

A 23 cc Teflon liner was charged with a 0.58M aqueous solution of 1-(decahydronaphthalen-2-yl)-1-methylpyrrolidinum hydroxide (3.9 g, 2.25 mmole), a 1M aqueous solution of NaOH (1.5 g) and deionized water (2.2. g). To this mixture, Na—Y zeolite (0.25 g) as the aluminum source and CAB-O-SIL® M-5 fumed silica (0.85 g) were added and thoroughly stirred until a homogenous mixture was obtained. The resulting gel was capped off and placed in a Parr steel autoclave and heated in an oven at about 160° C. while tumbling at about 43 rpm for 6-12 days. The reaction was surveyed by periodically monitoring the pH of the gel, and by looking for crystal growth using SEM. Once the crystallization was complete, the starting reaction gel turned into a clear liquid layer and a fine powdery precipitate. The mixture was filtered through a fritted-glass funnel. The collected solids were thoroughly washed with deionized water and, then, rinsed with acetone (~20 mL) to remove any organic residues. The solids were allowed to air-dry overnight and, then, dried in an oven at 120° C. for 2 hours.

Figure 5:
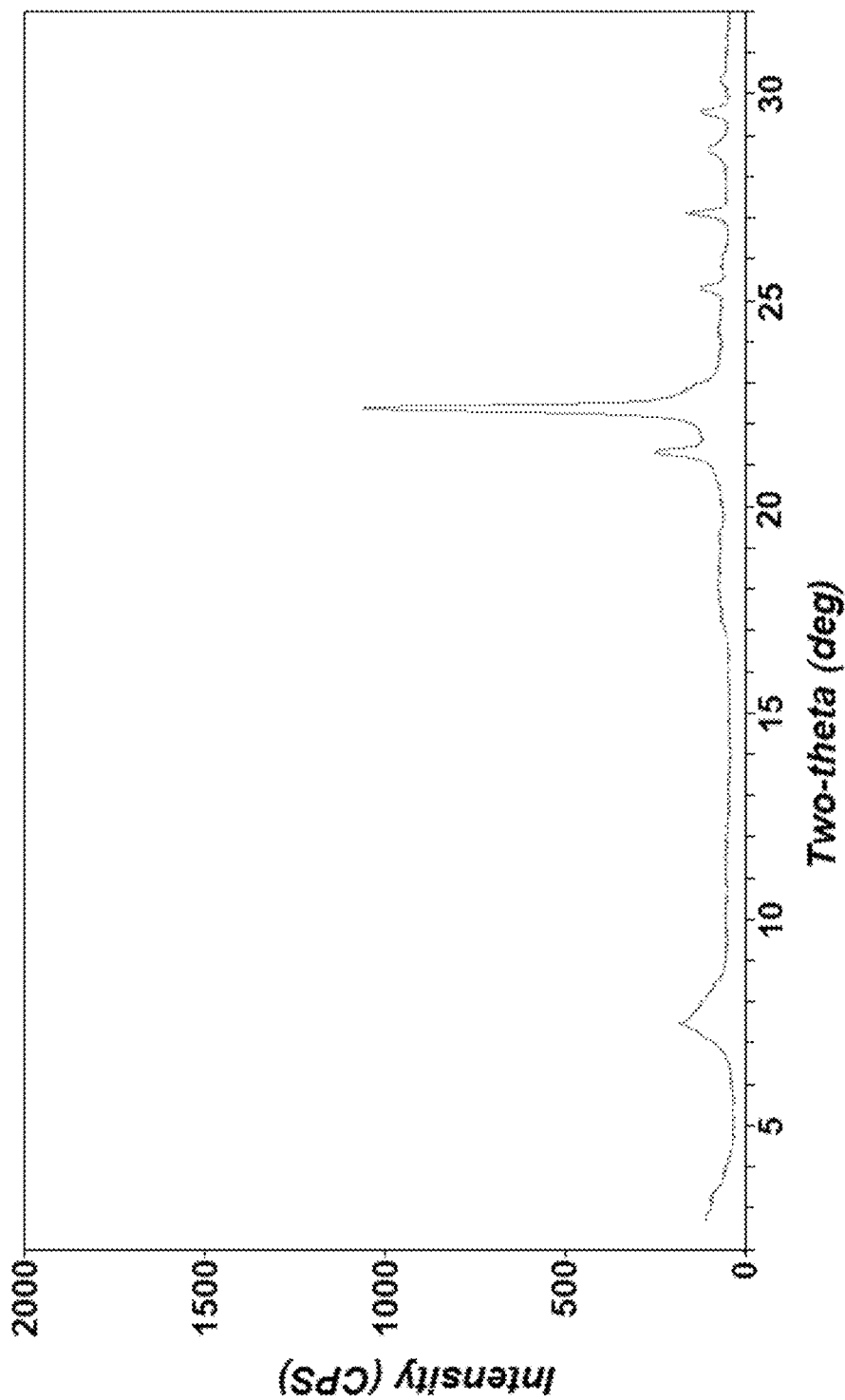
FIG. 5 is a powder XRD pattern of the as-synthesized aluminosilicate molecular sieve prepared in Example 4.
Figure 6:
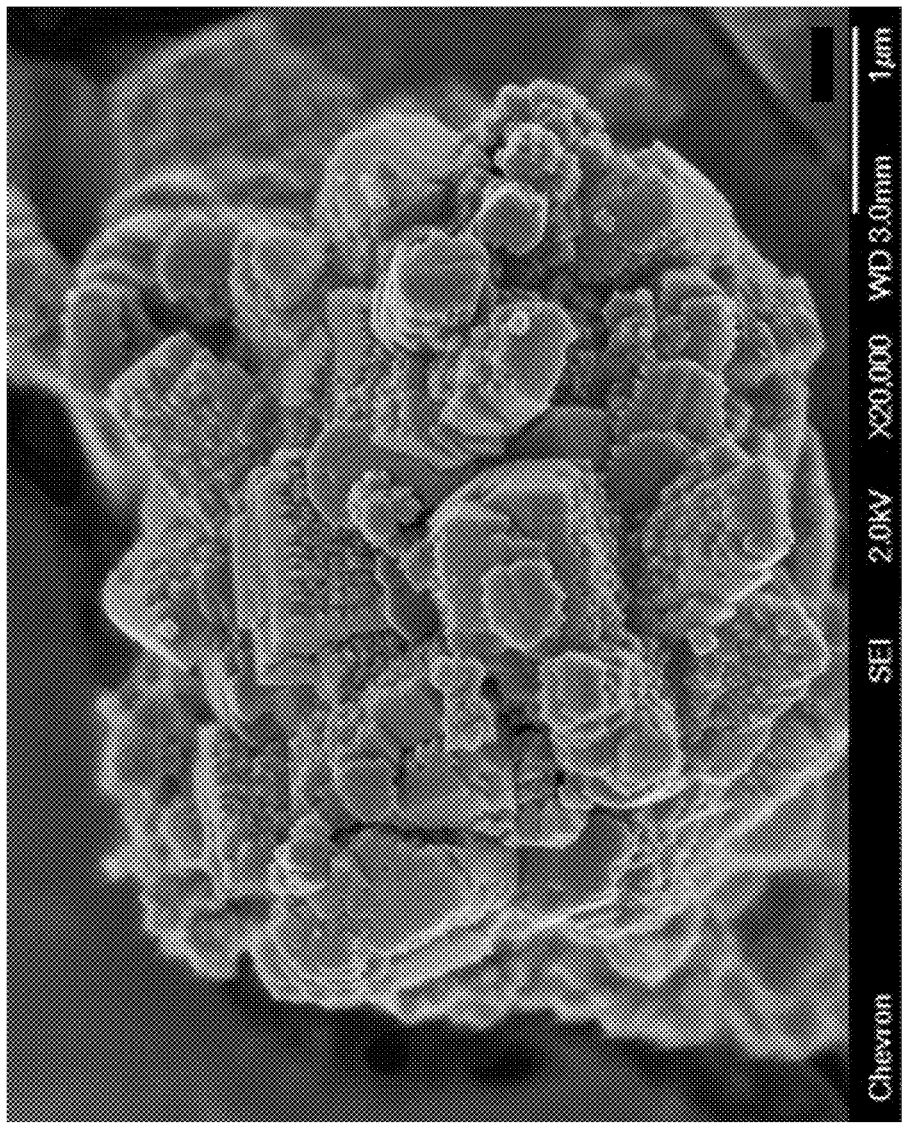
FIG. 6 is a SEM image of the as-synthesized aluminosilicate molecular sieve prepared in Example 4.

The resulting as-synthesized product was analyzed by powder XRD and SEM. FIG. 5 is the powder XRD pattern of the product, which showed the product to be SSZ-63. Table 7 below shows the powder XRD lines for the product. FIG. 6 shows a SEM image of the product. The reaction afforded about 0.81 g of aluminosilicate SSZ-63.

TABLE 7

| 2-Theta | d-spacing (nm) | Relative Intensity[a] |
|---|---|---|
| 7.46 | 1.184 | S |
| 21.31 | 0.417 | M |
| 22.39 | 0.397 | VS |
| 25.30 | 0.352 | W |
| 27.12 | 0.328 | W |
| 28.64 | 0.311 | W |
| 29.56 | 0.302 | W |
| 33.30 | 0.269 | W |

[a]The powder X-ray diffraction patterns provided are based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

Example 5

Seeded Synthesis of B-SSZ-63

Example 2 was repeated as described above except that B-SSZ-63 seed crystals (60 mg) from a previous synthesis were added to the reaction mixture and the reaction mixture was heated at 160° C. for 5 days. The recovered product was pure B-SSZ-63, as determined by powder XRD and SEM.

Example 6

Seeded Synthesis of Al-SSZ-63

Example 3 above was repeated as described above except that Al-SSZ-63 seed crystals (60 mg) from a previous synthesis were added to the reaction mixture and the reaction mixture was heated for 6 days at 170° C. The recovered product was pure Al-SSZ-63 (0.91 g), as determined by powder XRD and SEM.

Example 7

Seeded Synthesis of Al-SSZ-63

Example 4 above was repeated as described above except that Al-SSZ-63 seed crystals (60 mg) from a previous synthesis were added to the reaction mixture. The reaction mixture was heated for 6 days at 170° C. to provide pure Al-SSZ-63 (0.94 g), as determined by powder XRD and SEM.

Example 8

Calcination of B-SSZ-63

Figure 7:
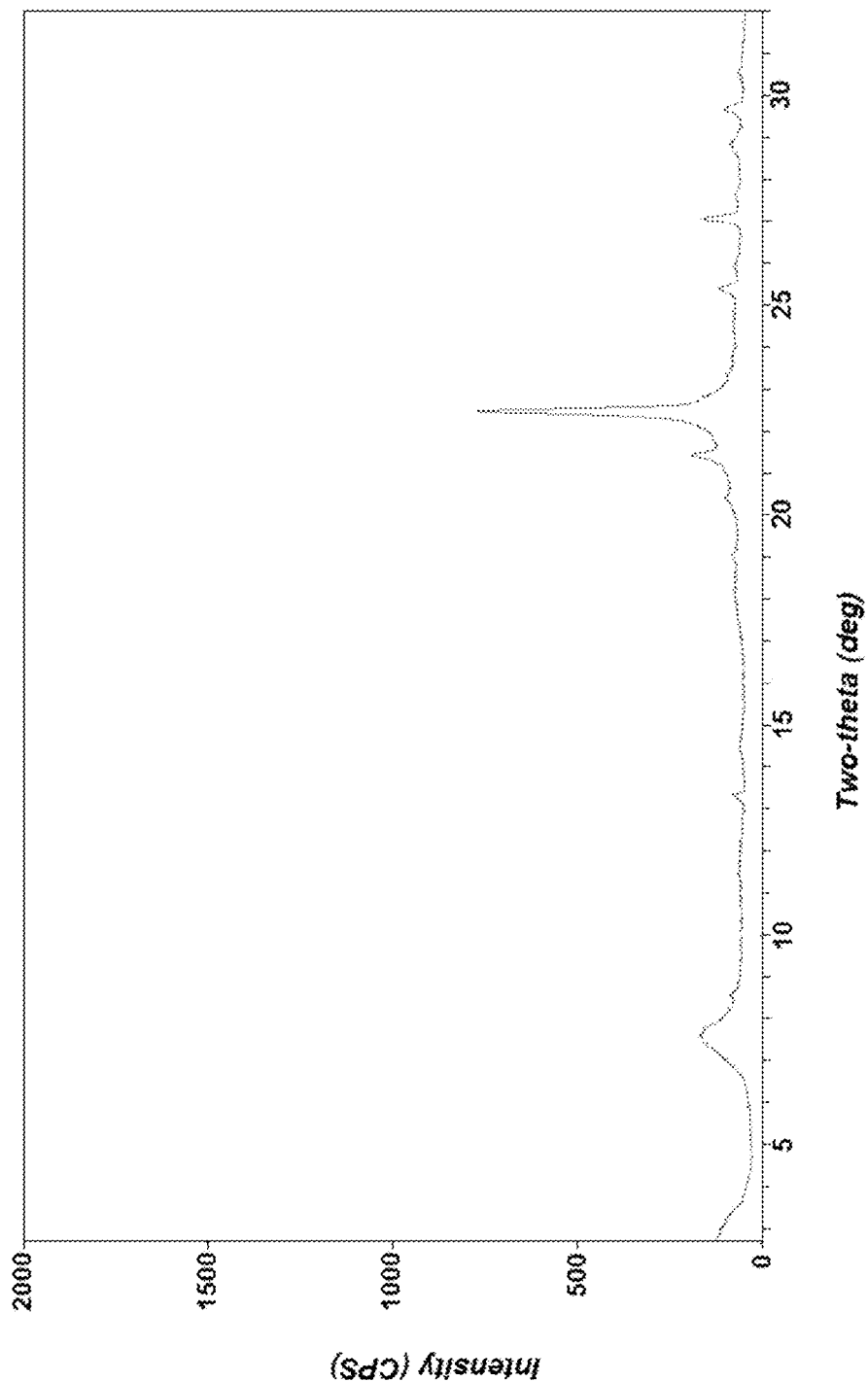
FIG. 7 is a powder XRD pattern of the calcined borosilicate molecular sieve prepared in Example 8.

The as-synthesized borosilicate SSZ-63 of Example 2 was calcined in nitrogen with an oxygen bleed in a muffle furnace from room temperature to 120° C. at a rate of 1° C./minute and held at 120° C. for 2 hours. The temperature was then ramped up to 540° C. at a rate of 1° C./minute and held at 540° C. for 5 hours. The temperature was then increased at the same rate (1° C./min) to 595° C. and held at 595° C. for 5 hours. The powder XRD pattern of the calcined molecular sieve is shown in FIG. 7 and indicates that the material remains stable after calcination to remove the organic structure directing agent (22 wt. % loss). Table 8 below shows the powder XRD lines for the calcined material.

TABLE 8

| 2-Theta | d-spacing (nm) | Relative Intensity[a] |
|---|---|---|
| 7.70 | 1.149 | VS |
| 8.56 | 1.032 | W |
| 13.34 | 0.663 | W |
| 19.04 | 0.466 | W |
| 20.39 | 0.435 | W |
| 21.40 | 0.415 | M |
| 22.48 | 0.395 | VS |
| 25.40 | 0.350 | W |
| 27.06 | 0.329 | W |
| 27.63 | 0.323 | W |
| 28.85 | 0.309 | W |
| 29.66 | 0.301 | W |
| 33.56 | 0.267 | W |

[a]The powder X-ray diffraction patterns provided are based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

The micropore volume and external surface area of calcined B-SSZ-63 were then measured by nitrogen physisorption using the B.E.T. method. The calcined B-SSZ-63 had a micropore volume of 0.23 cm$^3$/g, an external surface area of 65.7 m$^2$/g, and a B.E.T. surface area of 549.3 m$^2$/g.

The calcined B-SSZ-63 material had a $SiO_2/B_2O_3$ molar ratio of 52, as determined by ICP elemental analysis.

Example 9

Calcination of Al-SSZ-63

Figure 8:
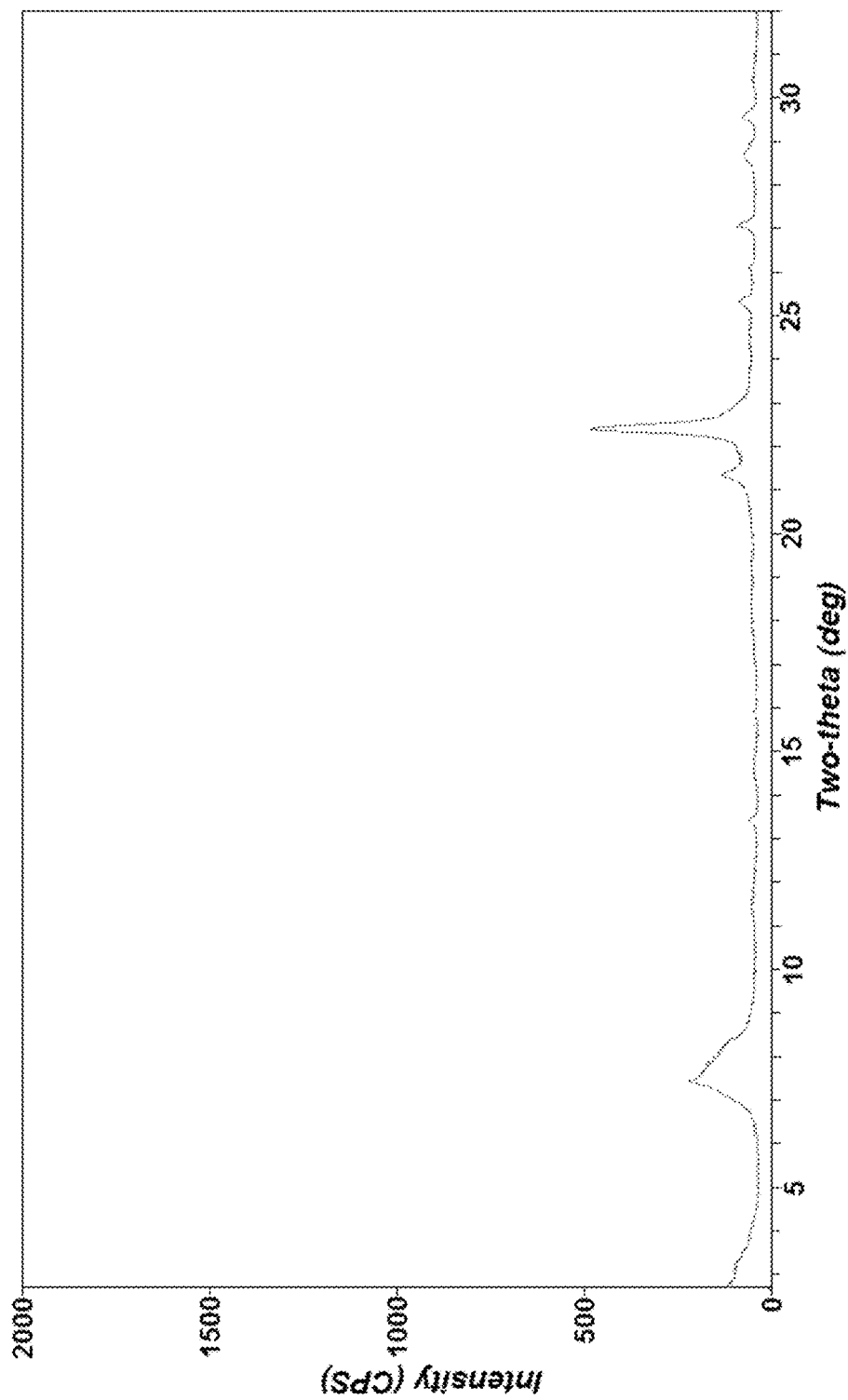
FIG. 8 is a powder XRD pattern of the calcined aluminosilicate molecular sieve prepared in Example 9.

The as-synthesized aluminosilicate SSZ-63 of Example 4 was calcined in air in a muffle furnace from room temperature to 120° C. at a rate of 1° C./minute and held at 120° C. for 2 hours. The temperature was then ramped up to 540° C. at a rate of 1° C./minute and held at 540° C. for 5 hours. The temperature was then increased at the same rate (1° C./min) to 595° C. and held at 595° C. for 5 hours. The powder XRD pattern of the calcined zeolite is shown in FIG. 8 and indicates that the material remains stable after calcination to remove the organic SDA (18.5 wt. % loss). Table 9 below shows the powder XRD lines for the calcined material.

TABLE 9

| 2-Theta | d-spacing (nm) | Relative Intensity[a] |
|---|---|---|
| 7.43 | 1.188 | VS |
| 8.29 | 1.066 | VS |
| 13.44 | 0.658 | W |
| 21.34 | 0.416 | W |
| 22.39 | 0.398 | VS |
| 25.32 | 0.352 | W |
| 26.10 | 0.341 | W |
| 27.05 | 0.329 | W |
| 28.71 | 0.311 | W |
| 29.54 | 0.302 | W |
| 33.37 | 0.268 | W |

[a]The powder X-ray diffraction patterns provided are based on a relative intensity scale in which the strongest line in the XRD pattern is assigned a value of 100: W = weak (>0 to ≤20); M = medium (>20 to ≤40); S = strong (>40 to ≤60); VS = very strong (>60 to ≤100).

The micropore volume and external surface area of calcined Al-SSZ-63 were then measured by nitrogen physisorption using the B.E.T. method. The calcined Al-SSZ-63 had a micropore volume of 0.24 cm$^3$/g, an external surface area of 70.4 m$^2$/g, and a B.E.T. surface area was 593.5 m$^2$/g. This calcined Al-SSZ-63 material had a $SiO_2/Al_2O_3$ molar ratio of 36.2, as determined by ICP elemental analysis.

The calcined Al-SSZ-63 of Example 3 had a micropore volume of 0.21 cm$^3$/g, an external surface area of 181 m$^2$/g, and a B.E.T. surface area of 571.5 m²/g. This calcined Al-SSZ-63 material had a SiO$_2$/Al$_2$O$_3$ mole ratio of 68, as determined by ICP elemental analysis.

The invention claimed is:

1. A method of synthesizing a molecular sieve having the structure of SSZ-63, the method comprising:
   (a) preparing a reaction mixture comprising:
      (1) a source of silicon oxide;
      (2) a source of an oxide of a trivalent element (X);
      (3) a source of a Group 1 or 2 metal (M);
      (4) a structure directing agent (Q) comprising 1-(decahydronaphthalen-2-yl)-1-methylpyrrolidinium cations;
      (5) hydroxide ions;
      (6) water; and
   (b) subjecting the reaction mixture to crystallization conditions sufficient to form crystals of the molecular sieve.

2. The method of claim 1, wherein the reaction mixture has a composition, in terms of molar ratios, as follows:

| | |
|---|---|
| SiO$_2$/X$_2$O$_3$ | 10 to 200 |
| M/SiO$_2$ | 0.05 to 0.40 |
| Q/SiO$_2$ | 0.05 to 0.50 |
| OH/SiO$_2$ | 0.10 to 0.50 |
| H$_2$O/SiO$_2$ | 10 to 80. |

3. The method of claim 1, wherein the reaction mixture has a composition, in terms of molar ratios, as follows:

| | |
|---|---|
| SiO$_2$/X$_2$O$_3$ | 15 to 100 |
| M/SiO$_2$ | 0.10 to 0.30 |
| Q/SiO$_2$ | 0.10 to 0.30 |
| OH/SiO$_2$ | 0.15 to 0.40 |
| H$_2$O/SiO$_2$ | 15 to 60. |

4. The method of claim 1, wherein the trivalent element X is selected from one or more of boron, aluminum, gallium, and iron.

5. The method of claim 1, wherein the trivalent element X is selected from one or more of boron and aluminum.

6. The method of claim 1, wherein the crystallization conditions include a temperature of from 125° C. to 200° C.

7. A molecular sieve having the structure of SSZ-63 and comprising 1-(decahydronaphthalen-2-yl)-1-methylpyrrolidinium cations in its pores.

8. The molecular sieve of claim 7, having, in its as-synthesized and anhydrous form, a composition, in terms of molar ratios, as follows:

| | |
|---|---|
| SiO$_2$/X$_2$O$_3$ | 10 to 200 |
| Q/SiO$_2$ | >0 to 0.2 |
| M/SiO$_2$ | >0 to 0.2 | wherein X is a trivalent element; Q comprises 1-(decahydronaphthalen-2-yl)-1-methylpyrrolidinium cations; and M is a Group 1 or 2 metal.

9. The molecular sieve of claim 8, wherein the trivalent element X is selected from one or more of boron, aluminum, gallium, and iron.

10. The molecular sieve of claim 8, wherein the trivalent element X is selected from one or more of boron and aluminum.

* * * * *